(12) United States Patent
Miyawaki et al.

(10) Patent No.: US 7,541,451 B2
(45) Date of Patent: Jun. 2, 2009

(54) **FLUORESCENT PROTEINS FROM *FUNGIA***

(75) Inventors: Atsushi Miyawaki, Wako (JP); Satoshi Karasawa, Tokyo (JP)

(73) Assignees: RIKEN, Saitama (JP); Medical & Biological Laboratories Co., Ltd., Aichi (JP)

( * ) Notice: Subject to any disclaimer, the term of this patent is extended or adjusted under 35 U.S.C. 154(b) by 155 days.

(21) Appl. No.: 11/739,133

(22) Filed: Apr. 24, 2007

(65) Prior Publication Data

US 2008/0166799 A1 Jul. 10, 2008

Related U.S. Application Data

(62) Division of application No. 10/498,505, filed as application No. PCT/JP02/13363 on Dec. 20, 2002, now Pat. No. 7,226,993.

(30) Foreign Application Priority Data

Dec. 20, 2001 (JP) ............................. 2001-387510

(51) Int. Cl.
*C07H 21/04* (2006.01)
*C07K 14/00* (2006.01)
(52) U.S. Cl. .................. 536/23.1; 530/350; 530/400
(58) Field of Classification Search ................. 536/23.1; 530/350
See application file for complete search history.

(56) References Cited

U.S. PATENT DOCUMENTS

2003/0017538 A1    1/2003    Miyawaki et al.

FOREIGN PATENT DOCUMENTS

| EP | 1464701 | 10/2004 |
|---|---|---|
| WO | 00/34320 | 6/2000 |
| WO | 00/34526 | 6/2000 |
| WO | 01/27150 | 4/2001 |
| WO | 03/033693 | 4/2003 |
| WO | 03/054191 | 7/2003 |
| WO | 03/070952 | 8/2003 |

OTHER PUBLICATIONS

R.Y. Tsien, Ann. Rev. Biochem., vol. 67, pp. 509-544, 1998.
M.V. Matz et al., Nat. Biotechnol., vol. 17, No. 10, pp. 969-973, 1999.
K.A. Lukyanov et al., J. Biol. Chem. ,vol. 275, No. 34, pp. 25879-25882, 2000.
T. Hosaka, Kagaku to Kogyo, vol. 53, No. 5, pp. 612, 2000.
A.F. Fradkov et al., FEBS Letters, vol. 479, No. 3, pp. 127-130, 2000.
A.A. Heikal et al., Proc. Natl. Acad. Sci. USA, vol. 97, No. 22, pp. 11996-12001, 2000.
Oz Reef Press. Resident of the Month, Oz Reef Marine Park, Jun. 1998, retrieved on Mar. 3, 2003 from http://ozreef.org/press/1998/june.html.
Oz Reef Press. Resident of the Month, Oz Reef Marine Park ,Jun. 1998, retrieved on May 1997 from http://ozreef.org/press/1997/may.html.
U.S. Appl. No. 10/492,081 (Miyawaki et al.), filed Feb. 25, 2003, which is national stage of PCT/JP02/10529.
U.S. Appl. No. 10/504,325 (Miyawaki et al.), filed Oct. 10, 2002, which is national stage of PCT/JP03/02033.
U.S. Appl. No. 10/581,551 (Miyawaki et al.), filed Jun. 2, 2006.
U.S. Appl. No. 11/390,215 (Miyawaki et al.), filed Mar. 28, 2006.
A.Salih et al., Nature, vol. 408, No. 6814, Dec. 14, 2000, pp. 850-853.
N. Gurskaya et al., BMC Biochemistry, vol. 2, No. 6, Jul. 10, 2001, pp. 1-7.
Y. Labas et al., "Diversity and Evolution of the Green Fluorescent Protein Family", Proc. Nat. Acad. Sci., vol. 99, No. 7, pp. 4256-4261 (2002).
S. Karasawa et al., "Cyan-Emitting and Orange-Emitting Fluprescent Proteins as a Donor/Aceeptor Pair for Fluorescence Resonance Energy Transfer", Biochemical Journal, vol. 381, No. 1, pp. 307-312 (2004).

*Primary Examiner*—Suzanne M. Noakes
(74) *Attorney, Agent, or Firm*—Greenblum & Bernstein, P.L.C.

(57) ABSTRACT

An object of the present invention is to provide a novel fluorescent protein derived from organisms other than *Aequorea victoria*. According to the present invention, there is provided a fluorescent protein derived from *Fungia* sp., which has the following properties:
(1) the excitation maximum wavelength is 455 nm, and the fluorescence maximum wavelength is 488 nm;
(2) the molar absorption coefficient at 455 nm is 38700 or 27700;
(3) the quantum yield is 0.85 or 0.81; and
(4) the pH sensitivity of the fluorescent property is stable at pH 5 to 9; and
a fluorescent protein derived from *Fungia* sp., which has the following properties:
(1) the excitation maximum wavelength is 548 nm, and the fluorescence maximum wavelength is 561 nm;
(2) the molar absorption coefficient at 548 nm is 75900 or 51000;
(3) the quantum yield is 0.44 or 0.50; and
(4) the pH sensitivity of the fluorescent property is pKa<5.0.

8 Claims, 6 Drawing Sheets

2-1

2-2

2-3

FLUORESCENT PROTEINS FROM *FUNGIA*

CROSS-REFERENCE TO RELATED APPLICATIONS

This application is a divisional of application Ser. No. 10/498,505, filed Nov. 22, 2004, now U.S. Pat. No. 7,226,993, which is a National Stage Application of International Application No. PCT/JP02/13363, filed Dec. 20, 2002, which was not published in English under PCT Article 21(2), entering the National Stage on Jun. 18, 2004, and which claims priority of Japanese Application No. 2001-387510, filed Dec. 20, 2001. The entire disclosure of application Ser. No. 10/498,505, now U.S. Pat. No. 7,226,993, is considered as being part of this application, and the entire disclosure of application Ser. No. 10/498,505, now U.S. Pat. No. 7,226,993, is expressly incorporated by reference herein in its entirety.

TECHNICAL FIELD

The present invention relates to a novel fluorescent protein having improved properties. More specifically, the present invention relates to a novel fluorescent protein derived from *Fungia* sp., and the use thereof.

BACKGROUND ART

Green fluorescent protein (GFP) derived from *Aequorea victoria*, a jellyfish, has many purposes in biological systems. Recently, various GFP mutants have been produced based on the random mutagenesis and semi-rational mutagenesis, wherein a color is changed, a folding property is improved, luminance is enhanced, or pH sensitivity is modified. Fluorescent proteins such as GFP are fused with other proteins by gene recombinant technique, and monitoring of the expression and transportation of the fusion proteins is carried out.

One of the most commonly used types of GFP mutant is Yellow fluorescent protein (YFP). Among Aequorea-derived GFP mutants, YFP exhibits the fluorescence with the longest wavelength. The values $\epsilon$ and $\Phi$ of the majority of YEPs are 60,000 to 100,000 $M^{-1}$ $cm^{-1}$ and 0.6 to 0.8, respectively (Tsien, R. Y. (1998). Ann. Rev. Biochem. 67, 509-544). These values are comparable to those of the general fluorescent group (fluorescein, rhodamine, etc.). Accordingly, improvement of the absolute luminance of YFP is nearly approaching its limit.

Moreover, Cyan fluorescent protein (CFP) is another example of GFP mutants. Among such Cyan fluorescent proteins, ECFP (enhanced cyan fluorescent protein) has been known. Furthermore, Red fluorescent protein (RFP) has been isolated from sea anemone (*Discoma* sp.), and among such red fluorescent proteins, DasRed has been known. Thus, 4 types of fluorescent proteins including green, yellow, cyan and red fluorescent proteins, have been developed one after another, and their spectrum range has been significantly extended.

DISCLOSURE OF THE INVENTION

An object of the present invention is to provide a novel fluorescent protein derived from organisms other than *Aequorea victoria* and sea anemone. Another object of the present invention is to provide a novel fluorescent protein having improved fluorescent properties as compared with the fluorescent protein derived from *Aequorea victoria* or sea anemone.

In order to achieve the above objects, the present inventors have noticed fluorescent corals, and have conducted intensive studies to obtain a gene of fluorescent protein from corals by using suitable primers designed based on the amino acid sequences of known fluorescent proteins. As a result, they have succeeded in amplifying and cloning genes of fluorescent proteins from the cDNA library of *Fungia* sp., a coral which is different from *Galaxea fascicularis* from which a gene of a fluorescent protein was previously obtained, using the above primers. Further, the present inventors have examined the fluorescent properties of the obtained fluorescent proteins derived from *Fungia* sp. and as a result, they have found that these fluorescent proteins have desired fluorescent properties. The present invention has been completed based on these findings.

Thus, the present invention provides a fluorescent protein derived from *Fungia* sp., which has the following properties:

(1) the excitation maximum wavelength is 455 nm, and the fluorescence maximum wavelength is 488 nm;

(2) the molar absorption coefficient at 455 nm is 38700 or 27700;

(3) the quantum yield is 0.85 or 0.81; and (4) the pH sensitivity of the fluorescent property is stable at pH 5 to 9.

The present invention further provides a fluorescent protein derived from *Fungia* sp., which has the following properties:

(1) the excitation maximum wavelength is 548 nm, and the fluorescence maximum wavelength is 561 nm;

(2) the molar absorption coefficient at 548 nm is 75900 or 51000;

(3) the quantum yield is 0.44 or 0.50; and (4) the pH sensitivity of the fluorescent property is pKa<5.0.

In another aspect of the present invention, there is provided a fluorescent protein of the following (a) or (b):

(a) a protein having an amino acid sequence shown in SEQ ID NO: 1 or 2; or (b) a protein having an amino acid sequence comprising a deletion, substitution and/or addition of one or several amino acids with respect to the amino acid sequence shown in SEQ ID NO: 1 or 2, and having fluorescent properties which are equivalent to those of a protein having an amino acid sequence shown in SEQ ID NO: 1 or 2.

Further, in another aspect of the present invention, there is provided a fluorescent protein of the following (a) or (b):

(a) a protein having an amino acid sequence shown in SEQ ID NO: 3 or 4; or (b) a protein having an amino acid sequence comprising a deletion, substitution and/or addition of one or several amino acids with respect to the amino acid sequence shown in SEQ ID NO: 3 or 4, and having fluorescent properties which are equivalent to those of a protein having an amino acid sequence shown in SEQ ID NO: 3 or 4.

In further another aspect of the present invention, there is provided a protein having an amino acid sequence wherein cysteine at position 64 is substituted with alanine with respect to the amino acid sequence shown in SEQ ID NO: 3, or an amino acid sequence wherein glutamic acid at position 211 is substituted with alanine with respect to the amino acid sequence shown in SEQ ID NO: 3.

In further another aspect of the present invention, there is provided DNA which encodes the fluorescent protein of the present invention as mentioned above.

In further another aspect of the present invention, there is provided DNA which encodes the protein of the following (a) or (b):
(a) a protein having an amino acid sequence shown in SEQ ID NO: 1 or 2; or
(b) a protein having an amino acid sequence comprising a deletion, substitution and/or addition of one or several amino acids with respect to the amino acid sequence shown in SEQ ID NO: 1 or 2, and having fluorescent properties which are equivalent to those of a protein having an amino acid sequence shown in SEQ ID NO: 1 or 2.

In further another aspect of the present invention, there is provided DNA which encodes the protein of (a) or (b):
(a) a protein having an amino acid sequence shown in SEQ ID NO: 3 or 4; or
(b) a protein having an amino acid sequence comprising a deletion, substitution and/or addition of one or several amino acids with respect to the amino acid sequence shown in SEQ ID NO: 3 or 4, and having fluorescent properties which are equivalent to those of a protein having an amino acid sequence shown in SEQ ID NO: 3 or 4.

In further another aspect of the present invention, there is provided DNA of the following (a) or (b):
(a) DNA having a nucleotide sequence shown in SEQ ID NO: 5 or 6; or
(b) DNA having a nucleotide sequence comprising a deletion, substitution and/or addition of one or several nucleotides with respect of the nucleotide sequence shown in SEQ ID NO: 5 or 6, and encoding a protein having fluorescent properties which are equivalent to those of a protein encoded by the nucleotide sequence shown in SEQ ID NO: 5 or 6.

In further another aspect of the present invention, there is provided DNA of the following (a) or (b):
(a) DNA having a nucleotide sequence shown in SEQ ID NO: 7 or 8; or
(b) DNA having a nucleotide sequence comprising a deletion, substitution and/or addition of one or several nucleotides with respect of the nucleotide sequence shown in SEQ ID NO: 7 or 8, and encoding a protein having fluorescent properties which are equivalent to those of a protein encoded by the nucleotide sequence shown in SEQ ID NO: 7 or 8.

In further another aspect of the present invention, there is provided a recombinant vector having the above-described DNA of the present invention.

In further another aspect of the present invention, there is provided a transformant having the above-described DNA or recombinant vector of the present invention.

In further another aspect of the present invention, there is provided a fusion fluorescent protein consisting of the above-described fluorescent protein of the present invention and another protein. Preferably, said another protein is one that localizes in the cell, and more preferably, said another protein is one specific to an intracellular organella.

In further another aspect of the present invention, there is provided a method for analyzing the localization or dynamics of a protein in cells, characterized in that the above-described fusion protein of the present invention is allowed to be expressed in cells.

In another aspect of the present invention, there is provided a fluorescent reagent kit which comprises the above-described fluorescent protein, DNA, recombinant vector, transformant or fusion protein according to the present invention.

BEST MODE FOR CARRYING OUT THE INVENTION

Figure 1:
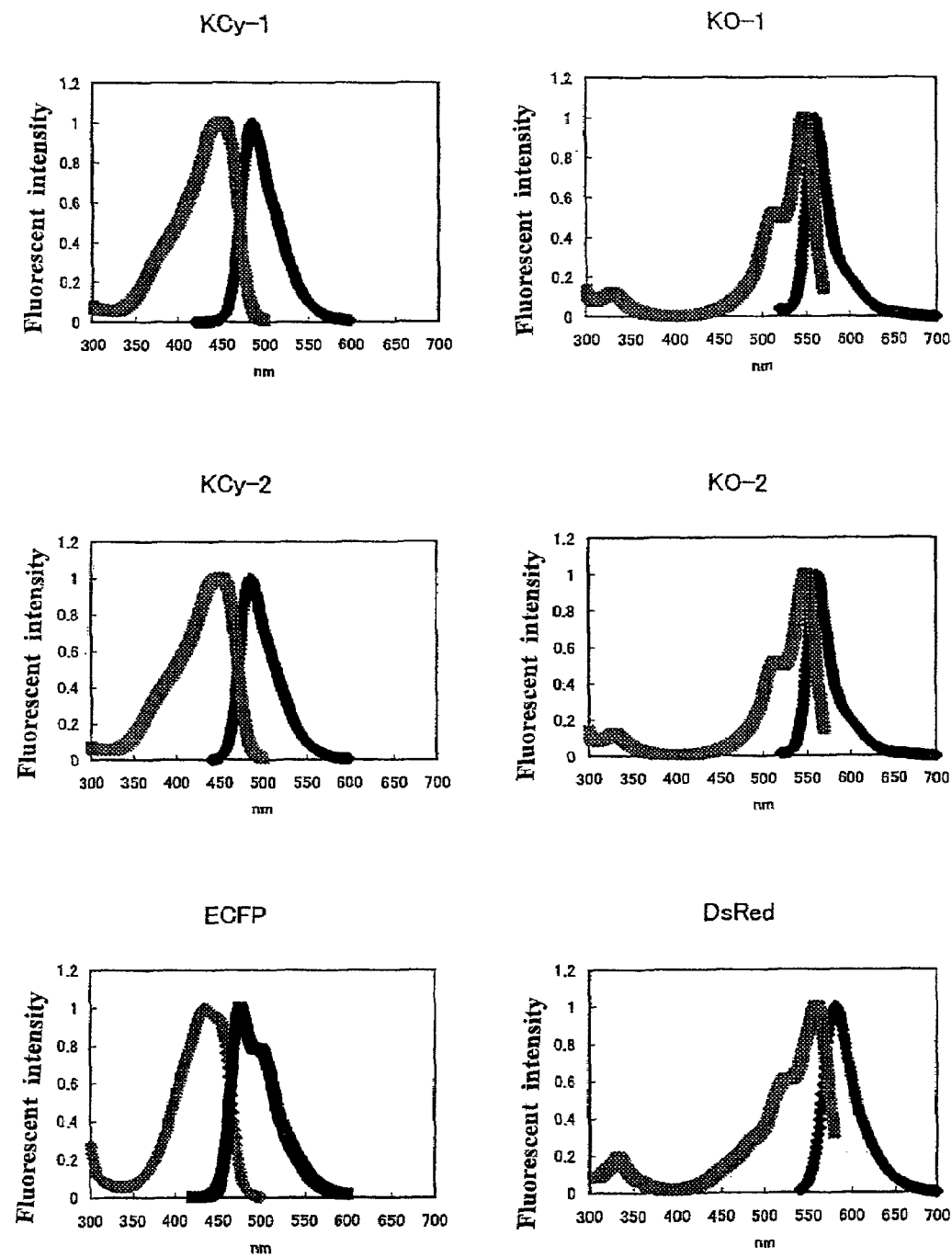
FIG. 1 shows results obtained by comparing the fluorescence spectrum and excitation spectrum of fluorescent proteins derived from *Fungia* sp. of the present invention (KCy-1 and KCy-2) with those of ECFP, and by comparing the fluorescence spectrum and excitation spectrum of fluorescent proteins derived from *Fungia* sp. of the present invention (KO-1 and KO-2) and those of DsRed.

The embodiments of the present invention will be described in detail below.

(1) Fluorescent Protein of the Present Invention

The fluorescent protein of the present invention is characterized in that it is derived from *Fungia* sp. and has the following properties:
(1) the excitation maximum wavelength is 455 nm, and the fluorescence maximum wavelength is 488 nm;
(2) the molar absorption coefficient at 455 nm is 38700 or 27700;
(3) the quantum yield is 0.85 or 0.81; and
(4) the pH sensitivity of the fluorescent property is stable at pH 5 to 9.

Another fluorescent protein of the present invention is characterized in that it is derived from *Fungia* sp. and has the following properties:
(1) the excitation maximum wavelength is 548 nm, and the fluorescence maximum wavelength is 561 nm;
(2) the molar absorption coefficient at 548 nm is 75900 or 51000;
(3) the quantum yield is 0.44 or 0.50; and
(4) the pH sensitivity of the fluorescent property is pKa<5.0.

*Fungia* sp. is one type of coral and mainly lives in the western region of the Atlantic Ocean. *Fungia* sp. is characterized in that the outer shape of a group of the corals is a polygon, having long tentacles, and that a group of the corals as a whole develops a clear orange color.

In Examples of the present specification described later, the fluorescent protein of the present invention having the above properties was isolated by using *Fungia* sp. as a starting material. However, in some cases, the fluorescent protein of the present invention can be obtained also from coral which emits fluorescence other than *Fungia* sp. Such fluorescent proteins are also included in the scope of the present invention.

As described in Examples mentioned later, the first fluorescent protein (KCy-1) of the present invention has an excitation maximum wavelength of 455 nm and a fluorescence maximum wavelength of 488 nm. It has a molar absorption coefficient of 38700 (455 nm) and a quantum yield of 0.85. As described in Examples mentioned later, the second fluorescent protein (KCy-2) of the present invention has an excitation maximum wavelength of 455 nm and a fluorescence maximum wavelength of 488 nm. It has a molar absorption coefficient of 27700 (455 nm) and a quantum yield of 0.81. In contrast, ECFP (Clontech) has a molar absorption coefficient of 28700 (435 mm) and a quantum yield of 0.40.

As described in Examples mentioned later, the third fluorescent protein (KO-1) of the present invention has an excitation maximum wavelength of 548 nm and a fluorescence maximum wavelength of 561 nm. It has a molar absorption coefficient of 75900 (548 nm) and a quantum yield of 0.44. As described in Examples mentioned later, the fourth fluorescent protein (KO-2) of the present invention has an excitation maximum wavelength of 548 nm and a fluorescence maximum wavelength of 561 nm. It has a molar absorption coefficient of 51000 (548 nm) and a quantum yield of 0.50. In contrast, DsRed (Clontech) has a molar absorption coefficient of 86100 (559 nm) and a quantum yield of 0.29.

Molar absorption coefficient represents the absorption amount of photons per mole of fluorescent molecules. Quantum yield is a numerical value showing the amount of the absorbed photons that can be emitted as fluorescence. Thus, when the values of the molar absorption coefficient and quantum yield are great, it shows that strong fluorescence is emitted. Accordingly, among the above-described fluorescent proteins of the present invention, since cyan fluorescent proteins KCy-1 and KCy-2 have a molar absorption coefficient and a quantum yield greater than those of ECFP, these proteins emit fluorescence stronger than that of ECFP. More specifically, KCy-1 emits fluorescence approximately 2 or 3 times brighter than that of ECFP, and KCy-2 emits fluorescence approximately 1.5 times brighter than that of ECFP.

With regard to the maximum excitation wavelength and the maximum fluorescence wavelength, there are no significant differences between ECFP and the fluorescent proteins KCy-1 and KCy-2 of the present invention. However, differing from ECFP, the excitation and fluorescence spectrums of the fluorescent proteins KCy-1 and KCy-2 of the present invention do not have a shoulder on their long wavelength side, but they have a sharp form. Accordingly, it can be said that these fluorescent proteins are advantageously used in multicolor imaging or the like which is performed in combination with other fluorescent molecules.

Moreover, KCy-1 and KCy-2 are characterized in that their fluorescence is low sensitive to pH in the range between pH 5 and pH 9. This is to say, there is only a slight extent of fluctuation in the peak value of their fluorescence intensity in the range between pH 5 and pH 9, and a high fluorescence intensity can be maintained in this pH range. In the case of the previously used ECFP, since its fluorescence intensity is decreased at pH 7 or lower, its use in living bodies has a certain limit. However, the fluorescent proteins of the present invention do not have such a limit.

On the other hand, orange fluorescent proteins KO-1 and KO-2 among the above-described fluorescent proteins of the present invention emit fluorescence approximately 2 times brighter than that of a red fluorescent protein (DsRed) derived from sea anemone (Discosoma). In addition, each of KO-1 and KO-2 has the peak of their fluorescence spectrum at a wavelength different from those of the existing fluorescent proteins. This is to say, EYFP (yellow) (Clontech) has the peak of its fluorescence spectrum around 530 nm, and DsRed (Clontech) has the peak of its fluorescence spectrum around 580 nm. In contrast, the KO-1 and KO-2 of the present invention has the peak of their fluorescence spectrum around 561 nm.

In addition, specific examples of a mutant of the protein KO-1 of the present invention may include:

(1) a mutant which is obtained by substituting cysteine at position 64 by alanine in the amino acid sequence of KO-1, and emits green fluorescence (fluorescence maximum at 508 nm, and excitation maximum at 496 nm), wherein the fluorescent properties are sifted on the short wavelength side when compared with KO; and (2) a mutant which is obtained by substituting glutamic acid at position 211 by alanine in the amino acid sequence of KO-1, and emits red fluorescence (fluorescence maximum at 578 nm, and excitation maximum at 563 nm), wherein fluorescent properties are sifted on the long wavelength side when compared with KO.

The examples of the fluorescent protein of the present invention include a fluorescent protein of the following (a) or (b):

(a) a protein having an amino acid sequence shown in SEQ ID NO: 1 or 2; or (b) a protein having an amino acid sequence comprising a deletion, substitution and/or addition of one or several amino acids with respect to the amino acid sequence shown in SEQ ID NO: 1 or 2, and having fluorescent properties which are equivalent to those of a protein having an amino acid sequence shown in SEQ ID NO: 1 or 2.

The further examples of the fluorescent protein of the present invention include a fluorescent protein of the following (a) or (b):

(a) a protein having an amino acid sequence shown in SEQ ID NO: 3 or 4; or (b) a protein having an amino acid sequence comprising a deletion, substitution and/or addition of one or several amino acids with respect to the amino acid sequence shown in SEQ ID NO: 3 or 4, and having fluorescent properties which are equivalent to those of a protein having an amino acid sequence shown in SEQ ID NO: 3 or 4.

The scope of "one or several" in the phrase "an amino acid sequence comprising a deletion, substitution and/or addition of one or several amino acids" used herein is not particularly limited in the present specification. For example, it means 1 to 20, preferably 1 to 10, more preferably 1 to 7, further preferably 1 to 5, and particularly preferably 1 to 3.

The term "fluorescent properties which are equivalent" used herein means that the protein has an equivalent fluorescence intensity, an equivalent excitation wavelength, an equivalent fluorescence wavelength, an equivalent pH sensitivity, or the like.

The method of obtaining the fluorescent protein of the present invention is not particularly limited. The protein may be either a protein synthesized by chemosynthesis, or recombinant protein produced by a gene recombination technique.

Where a recombinant protein is produced, it is necessary to obtain DNA encoding the protein. Appropriate primers are designed by utilizing information regarding the amino acid sequence shown in SEQ ID NOS: 1 to 4 of the sequence listing of the present specification and the nucleotide sequence shown in SEQ ID NOS: 5 to 8 thereof. Using these primers, PCR is carried out by using cDNA clones of the above-described various types of known fluorescent proteins as a template, so that DNA encoding the fluorescent protein of the present invention can be obtained. Where a partial fragment of DNA encoding the fluorescent protein of the present invention are obtained by the above-described PCR, the produced DNA fragments are ligated to one another by a gene recombination technique, so that DNA encoding the desired fluorescent protein can be obtained. The fluorescent protein of the present invention can be produced by introducing this DNA into an appropriate expression system. Expression in an expression system will be described later in the present specification.

(2) DNA of the Present Invention

According to the present invention, a gene encoding the fluorescent protein of the present invention is provided.

Specific examples of DNA encoding the fluorescent protein of the present invention may include DNA which encodes the protein of the following (a) or (b):
(a) a protein having an amino acid sequence shown in SEQ ID NO: 1 or 2; or
(b) a protein having an amino acid sequence comprising a deletion, substitution and/or addition of one or several amino acids with respect to the amino acid sequence shown in SEQ ID NO: 1 or 2, and having fluorescent properties which are equivalent to those of a protein having an amino acid sequence shown in SEQ ID NO: 1 or 2.

Further specific examples of DNA encoding the fluorescent protein of the present invention may include DNA which encodes the protein of the following (a) or (b):
(a) a protein having an amino acid sequence shown in SEQ ID NO: 3 or 4; or
(b) a protein having an amino acid sequence comprising a deletion, substitution and/or addition of one or several amino acids with respect to the amino acid sequence shown in SEQ ID NO: 3 or 4, and having fluorescent properties which are equivalent to those of a protein having an amino acid sequence shown in SEQ ID NO: 3 or 4.

Further specific examples of DNA encoding the fluorescent protein of the present invention may include DNA of the following (a) or (b):
(a) DNA having a nucleotide sequence shown in SEQ ID NO: 5 or 6; or
(b) DNA having a nucleotide sequence comprising a deletion, substitution and/or addition of one or several nucleotides with respect of the nucleotide sequence shown in SEQ ID NO: 5 or 6, and encoding a protein having fluorescent properties which are equivalent to those of a protein encoded by the nucleotide sequence shown in SEQ ID NO: 5 or 6.

Further specific examples of DNA encoding the fluorescent protein of the present invention may include DNA of the following (a) or (b):
(a) DNA having a nucleotide sequence shown in SEQ ID NO: 7 or 8; or
(b) DNA having a nucleotide sequence comprising a deletion, substitution and/or addition of one or several nucleotides with respect of the nucleotide sequence shown in SEQ ID NO: 7 or 8, and encoding a protein having fluorescent properties which are equivalent to those of a protein encoded by the nucleotide sequence shown in SEQ ID NO: 7 or 8.

The DNA of the present invention can be synthesized by, for example, the phosphoamidite method, or it can also be produced by polymerase chain reaction (PCR) using specific primers. The DNA of the present invention or a fragment thereof is produced by the method described above in the specification.

A method of introducing a desired mutation into a certain nucleic acid sequence is known to a person skilled in the art. For example, known techniques such as a site-directed mutagenesis, PCR using degenerated oligonucleotides, or the exposure of cells containing nucleic acid to mutagens or radioactive rays, are appropriately used, so as to construct DNA having a mutation. Such known techniques are described in, for example, Molecular Cloning: A Laboratory Manual, $2^{nd}$ Ed., Cold Spring Harbor Laboratory, Cold Spring Harbor, N.Y., 1989; and Current Protocols in Molecular Biology, Supplements 1 to 38, John Wiley & Sons (1987-1997).

(3) Recombinant Vector of the Present Invention

The DNA of the present invention can be inserted into a suitable vector and used. The type of a vector used in the present invention is not particularly limited. For example, it may be either a vector that can autonomously replicate (e.g., a plasmid, etc.), or vector that is incorporated into the genomes of host cells when it is introduced into the host cells and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows a transcriptional activity in host cells, and it is appropriately selected depending on the type of host cells.

Examples of a promoter which can operate in bacterial cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage rhamda, and lac, trp and tac promoters of *Escherichia coli*.

Examples of a promoter which can operate in mammalian cells may include an SV40 promoter, an MT-1 (metallothionein gene) promoter, and an adenovirus-2 major late promoter. Examples of a promoter which can operate in insect cells may include a polyhedrin promoter, a P10 promoter, an *Autographa californica* polyhedrosis basic protein promoter, a baculovirus immediate-early gene 1 promoter, and a baculovirus 39K delayed-early gene promoter. Examples of a promoter which can be operate in yeast host cells may include promoters derived from yeast glycolytic genes, an alcohol dehydrogenase gene promoter, a TPI1 promoter, and an ADH2-4c promoter.

Examples of a promoter which can operate in filamentous cells may include an ADH3 promoter and a tpiA promoter.

In addition, an appropriate terminator such as a human growth hormone terminator, or a TPI1 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent from host cells, such as a dihydrofolate reductase (DHFR) gene or a *Shizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(4) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria, yeasts, fungal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells. A method of transforming mammalian cells and expressing the introduced DNA sequence in the cells is also known. Examples of such a method may include the electroporation, the calcium phosphate method, and the lipofection method.

Examples of yeast cells may include those belonging to Saccharomyces or Shizosaccharomyces. Examples of such cells may include *Saccharomyces cerevisiae* and *Saccharomyces kluyveri*. Examples of a method of introducing a recombinant vector into yeast host cells may include the electroporation, the spheroplast method, and the lithium acetate method.

Examples of other fungal cells may include those belonging to *Filamentous fungi* such as *Aspergillus, Neurospora, Fusarium* or *Trichoderma*. Where *Filamentous fungi* are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus infecting to insects belonging to *Barathra brassicae*, can be used as baculovirus.

Examples of insect cells used herein may include Sf9 and Sf21, which are *Spodoptera frugiperda* ovarian cells [Baculovirus Expression Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus, may include the calcium phosphate method and the lipofection method.

The above transformant is cultured in an appropriate nutritive medium under conditions enabling the introduced DNA construct to be expressed. In order to isolate and purify the fusion fluorescent protein of the present invention from the culture product of the transformant, common methods of isolating and purifying proteins may be used.

For example, where the protein of the present invention is expressed in a state dissolved in cells, after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

(5) Use of the Fluorescent Protein of the Present Invention and a Fusion Fluorescent Protein Comprising the Same The fluorescent protein of the present invention can be fused with another protein, so as to construct a fusion fluorescent protein.

A method of obtaining the fusion fluorescent protein of the present invention is not particularly limited. It may be either a protein synthesized by chemosynthesis, or recombinant protein produced by a gene recombination technique.

Where a recombinant protein is produced, it is necessary to obtain DNA encoding the protein. Appropriate primers are designed by using the information regarding the amino acid sequence shown in SEQ ID NOS: 1 to 4 of the sequence listing of the present specification and the nucleotide sequence shown in SEQ ID NOS: 5 to 8 thereof. Using these primers, PCR is carried out using a DNA fragment containing the gene of the fluorescent protein of the present invention as a template, so as to produce DNA fragments necessary for construction of the DNA encoding the fluorescent protein of the present invention. Moreover, DNA fragments encoding a protein to be fused is also obtained in the same above manner.

Subsequently, the thus obtained DNA fragments are ligated to one another by a gene recombination technique, so that DNA encoding the desired fusion fluorescent protein can be obtained. This DNA is then introduced into an appropriate expression system, so that the fusion fluorescent protein of the present invention can be produced.

The fluorescent protein of the present invention has an extremely high utility value as a marker. This is to say, the fluorescent protein of the present invention is purified as a fusion protein with an amino acid sequence to be tested, and the fusion protein is introduced into cells by methods such as the microinjection. By observing the distribution of the fusion protein over time, targeting activity of the amino acid sequence to be tested can be detected in the cells.

The type of another protein (an amino acid sequence to be tested) with which the fluorescent protein of the present invention is fused is not particularly limited. Preferred examples may include proteins localizing in cells, proteins specific for intracellular organelles, and targeting signals (e.g., a nuclear transport signal, a mitochondrial presequence, etc.). In addition, the fluorescent protein of the present invention can be expressed in cells and used, as well as being introduced into cells by the microinjection or the like. In this case, a vector into which the DNA encoding the fluorescent protein of the present invention is inserted in such a way that it can be expressed, is introduced into host cells.

Moreover, the fluorescent protein of the present invention can also be used as a reporter protein to determine promoter activity. This is to say, a vector is constructed such that DNA encoding the fluorescent protein of the present invention is located downstream of a promoter to be tested, and the vector is then introduced into host cells. By detecting the fluorescence of the fluorescent protein of the present invention which is emitted from the cells, the activity of the promoter to be tested can be determined. The type of a promoter to be tested is not particularly limited, as long as it operates in host cells.

A vector used to detect the targeting activity of the above amino acid sequence to be tested or to determine promoter activity is not particularly limited. Examples of a vector preferably used for animal cells may include pNEO (P. Southern, and P. Berg (1982) J. Mol. Appl. Genet. 1: 327), pCAGGS (H. Niwa, K. Yamamura, and J. Miyazaki, Gene 108, 193-200 (1991)), pRc/CMV (manufactured by Invitrogen), and pCDM8 (manufactured by Invitrogen). Examples of a vector preferably used for yeasts may include pRS303, pRS304, pRS305, pRS306, pRS313, pRS314, pRS315, pRS316 (R. S. Sikorski and P. Hieter (1989) Genetics 122: 19-27), pRS423, pRS424, pRS425, pRS426 (T. W. Christianson, R. S. Sikorski, M. Dante, J. H. Shero, and P. Hieter (1992) Gene 110: 119-122).

In addition, the type of cells used herein is also not particularly limited. Various types of animal cells such as L cells, BalbC-3T3 cells, NIH3T3 cells, CHO (Chinese hamster ovary) cells, HeLa cells or NRK (normal rat kidney) cells, yeast cells such as *Saccharomyces cerevisiae*, *Escherichia coli* cells, or the like can be used. Vector can be introduced into host cells by common methods such as the calcium phosphate method or the electroporation.

The above obtained fusion fluorescent protein of the present invention wherein the fluorescent protein of the present invention is fused with another protein (referred to as a protein X) is allowed to be expressed in cells. By monitoring a fluorescence emitted, it becomes possible to analyze the localization or dynamics of the protein X in cells. That is, cells transformed or transfected with DNA encoding the fusion fluorescent protein of the present invention are observed with a fluorescence microscope, so that the localization and dynamics of the protein X in the cells can be visualized and thus analyzed.

For example, by using a protein specific for an intracellular organella as a protein X, the distribution and movement of a nucleus, a mitochondria, an endoplasmic reticulum, a Golgi body, a secretory vesicle, a peroxisome, etc., can be observed.

Moreover, for example, axis cylinders or dendrites of the nerve cells show an extremely complicated change in strikes in an individual who is under development. Accordingly, fluorescent labeling of these sites enables a dynamic analysis.

The fluorescence of the fluorescent protein of the present invention can be detected with a viable cell. Such detection can be carried out using, for example, a fluorescence microscope (Axiophoto Filter Set 09 manufactured by Carl Zeiss) or an image analyzer (Digital Image Analyzer manufactured by ATTO).

The type of a microscope can be appropriately selected depending on purposes. Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as a microscope system. When an erecting microscope with a high-powered lens is used, a water immersion lens can be used.

A filter set can be appropriately selected depending on the fluorescence wavelength of a fluorescent protein. In the case of the fluorescent protein having the excitation maximum wavelength of 455 nm and the fluorescence maximum wavelength of 488 nm among the fluorescent proteins of the present invention, a filter having an excitation light between approximately 440 and 460 nm and a fluorescence between approximately 480 and 520 nm can be preferably used. In the case of the fluorescent protein having the excitation maximum wavelength of 548 nm and the fluorescence maximum wavelength of 561 nm among the fluorescent proteins of the present invention, a filter having an excitation light between approximately 530 and 550 nm and a fluorescence between approximately 550 and 600 nm can be preferably used.

When viable cells are observed over time using a fluorescence microscope, a high sensitive cooled CCD camera is used, since photography is carried out in a short time. In the case of the cooled CCD camera, CCD is cooled to decrease thermal noise, so that a weak fluorescence image can be clearly photographed by exposure in a short time.

(6) Kit of the Present Invention

The present invention provides a kit for analyzing the localization of intracellular components and/or analyzing physiologically active substances, which is characterized in that it comprises at least one selected from the fluorescent protein, the fusion fluorescent protein, the DNA, the recombinant vector, or the transformant, which are described in the present specification. The kit of the present invention can be produced from commonly used materials that are known per se, by using common methods.

Reagents such as the fluorescent protein or the DNA are dissolved in an appropriate solvent, so that the reagents can be prepared in a form suitable for conservation. Water, ethanol, various types of buffer solution, etc. can be used as such a solvent.

The present invention will be further described in the following examples. However, the present invention is not limited by these examples.

EXAMPLES

Example 1

Isolation of a Novel Fluorescent Protein Gene From Coral (*Fungia* sp.)

(1) Extraction of Total RNA

A fluorescent protein gene was isolated from coral which emits a fluorescence. 2 individuals of *Fungia* sp. which have red or orange oral disc, were used as a material. *Fungia* sp. was crushed with a hammer. 7.5 ml of "TRIxol" (GIBCO BRL) was added to 4 g (wet weight) of the crushed coral, and the mixture was stirred, followed by centrifugal separation at 1,500×g for 10 minutes. 1.5 ml of chloroform was added to the obtained supernatant, and the mixture was stirred for 15 seconds, followed by leaving at rest for 3 minutes. Thereafter, the mixture was centrifuged at 7,500×g for 15 minutes. 3.75 ml of isopropanol was added to the obtained supernatant, and the mixture was stirred for 15 seconds, followed by leaving at rest for 10 minutes. Thereafter, the mixture was centrifuged at 17,000×g for 10 minutes. The obtained supernatant was discarded. 6 ml of 70% ethanol was added to the residue, and the mixture was centrifuged at 17,000×g for 10 minutes. The obtained supernatant was discarded, and the precipitate was then dissolved in 200 μl of DEPC water. Total RNA dissolved in the DEPC water was diluted 100 times, and the O.D.260 and O.D.280 values were measured to determine RNA concentration. 51.6 μg of the total RNA was obtained from the red individual, and 70 μg of the total RNA was obtained from the orange individual.

(2) Synthesis of First Strand cDNA cDNA (33 μl) was synthesized from 3 μg of the total RNA using a kit for synthesizing first strand cDNA "Ready To Go" (Amersham Pharmacia).

(3) Degenerated PCR

PCR was carried out using 3 μl of the synthesized first strand cDNA (33 μl) as a template. Primers were designed and produced such that regions similar to the amino acid sequences of known fluorescent proteins were picked up and such regions were converted into nucleotide sequences. The sequences of the used primers are shown below:

```
(primer 1)
                                          (SEQ ID NO: 9)
5'-GAAGGRTGYGTCAAYGGRCAY-3';
and (primer 2)
                                          (SEQ ID NO: 10)
5'-ACVGGDCCATYDGVAAGAAARTT-3'.
``` wherein R represents A or G, Y represents C or T, V represents A, C or G, and D represents A, G or T.

A PCR reaction solution having the following composition was used:

| | |
|---|---|
| Template (first strand cDNA) | 3 μl |
| ×10 taq buffer | 5 μl |
| 2.5 mM dNTPs | 4 μl |
| 100 μM primer 1 | 1 μl |
| 100 μM primer 2 | 1 μl |
| Milli-Q | 35 μl |
| Taq polymerase (5 U/μl) | 1 μl |

The following PCR reaction conditions were applied:

94° C.×1 minute (PAD)
94° C.×3 seconds (Denaturation)
52° C.×30 seconds (Annealing to template)
72° C.×1 minute (Primer elongation)

A cycle consisting of the above 3 steps was repeated 30 times. The annealing temperature was decreased by 0.3° C. each cycle. This is to say, the temperature was 43° C. when 30 cycles were completed.

72° C.×7 minutes (Final elongation)
4° C. (Retention)

Using 1 μl of the amplified product obtained in the first PCR reaction as a template, PCR was carried out again under the same conditions. A 350 bp band of the expected size was cut out and purified by agarose gel electrophoresis.

(4) Subcloning and Sequencing

The purified DNA fragment was ligated to a pT7-blue vector (Novagen). *Escherichia coli* (TG1) was transformed therewith and then subjected to blue white selection. Plasmid DNA was purified from white colonies *Escherichia coli*, and the nucleotide sequence of the inserted DNA fragment was determined using a DNA sequencer. Thereafter, the obtained nucleotide sequence was compared with the nucleotide sequences of other fluorescent protein genes, so as to judge whether or not the nucleotide sequence of the DNA fragment was derived from a fluorescent protein. With regard to those that were judged to be a part of the fluorescent protein genes, the full-length gene was cloned by the 5'-RACE method and the 3'-RACE method.

(5) 5'-RACE Method

In order to determine a nucleotide sequence on the 5'-side to the DNA fragment obtained by the Degenerated PCR, the 5'-RACE method was applied using 5'-RACE System for Rapid Amplification of cDNA Ends, Version 2.0 (GIBCO BRL). 3 μg of the total RNA prepared in (1) above was used as a template.

The following primers were used in the first amplification of dC-tailed cDNA of the orange individual:

```
                                          (SEQ ID NO: 11)
5'-GGCCACGCGTCGACTAGTACGGGIIGGGIIGGGIIG-3';
and
                                          (SEQ ID NO: 12)
5'-GGCTTATATGCGCACTGACTGC-3'
``` wherein I represents inosine.

The following primers were used in the second amplification:

```
5'-GGCCACGCGTCGACTAGTAC-3';       (SEQ ID NO: 13)
and
5'-TATCTCTTCAGGATATTTAGT-3'.       (SEQ ID NO: 14)
```

PCR reaction conditions were applied in accordance with protocols attached to the kit.

The amplified 700 bp band was cut out and purified by agarose gel electrophoresis. The purified DNA fragment was ligated to a pT7-blue vector (Novagen). *Escherichia coli* (TG1) was transformed therewith and then subjected to blue white selection. Plasmid DNA was purified from white colonies *Escherichia coli*, and the nucleotide sequence of the inserted DNA fragment was determined using a DNA sequencer.

In the same way, the following primers were used in the first amplification of dC-tailed cDNA of the red individual:

(SEQ ID NO: 15)
5'-GGCCACGCGTCGACTAGTACGGGIIGGGIIGGGIIG-3';
and (SEQ ID NO: 16)
5'-GGGAAAAGTGCCTTCAATGG-3' wherein I represents inosine.

The following primers were used in the second amplification:

5'-GGCCACGCGTCGACTAGTAC-3';   (SEQ ID NO: 17)
and

5'-TCTTCGAACTCAAACTTTCT-3'.   (SEQ ID NO: 18)

PCR reaction conditions were applied in accordance with protocols attached to the kit.

The amplified 500 bp band was cut out and purified by agarose gel electrophoresis. The purified DNA fragment was ligated to a pT7-blue vector (Novagen). *Escherichia coli* (TG1) was transformed therewith and then subjected to blue white selection. Plasmid DNA was purified from white colonies *Escherichia coli*, and the nucleotide sequence of the inserted DNA fragment was determined using a DNA sequencer.

(6) 3'-RACE Method

A nucleotide sequence on the 3'-side to the DNA fragment obtained by the Degenerated PCR was obtained by PCR, using the primer prepared based on the information obtained by determination of the nucleotide sequence in (4) above and an oligo dT primer. 3 µl of the first strand cDNA prepared in (2) above was used as a template.

The prepared primers were;

For orange individual;   5'-GCAGTCAGTGCG-CATATAAGCC-3' (primer3)(SEQ ID NO: 19)

For red individual;  5'-CCATTGAAGGCACTTTTCCC-3' (primer4) (SEQ ID NO: 20)

A PCR reaction solution having the following composition was used:

| | |
|---|---|
| Template (first strand cDNA) | 3 µl |
| x10 taq buffer | 5 µl |
| 2.5 mM dNTPs | 4 µl |
| 20 µM primer 3 or primer 4 | 1 µl |
| 10 µM oligo dT primer | 1 µl |
| Milli-Q | 35 µl |
| Taq polymerase (5 U/µl) | 1 µl |

The following PCR reaction conditions were applied:
94° C.×1 minute (PAD)
94° C.×30 seconds (Denaturation)
55° C.×30 seconds (Annealing to template)
72° C.×1 minute (Primer elongation)

A cycle consisting of the above 3 steps was repeated 30 times.
72° C.×7 minutes (Final elongation)
4° C. (Retention)

The amplified 850 bp band was cut and purified by agarose gel electrophoresis. The purified DNA fragment was ligated to a pT7-blue vector (Novagen). *Escherichia coli* (TG1) was transformed therewith and then subjected to blue white selection. Plasmid DNA was purified from white colonies *Escherichia coli*, and the nucleotide sequence of the inserted DNA fragment was determined using a DNA sequencer.

(7) Expression of Protein in *Escherichia coli*

From the obtained full-length nucleotide sequence, primers corresponding to the N-terminus and C-terminus of the protein were prepared. Thereafter, PCR was carried out using the first strand cDNA prepared in (2) above as a template. The used primer for both orange and red individuals is primer 5:

(primer 5)
(SEQ ID NO: 21)
5'-CGGGATCCATGAAGATGAAGTACTTTATGGATGG-3'

A PCR reaction solution having the following composition was used:

| | |
|---|---|
| Template (first strand cDNA) | 3 µl |
| x10 pyrobest buffer | 5 µl |
| 2.5 mM dNTPs | 4 µl |
| 20 µM primer 5 | 1 µl |
| 20 µM oligo dT primer | 1 µl |
| Milli-Q | 35 µl |
| Pyrobest polymerase (5 U/µl) | 1 µl |

The following PCR reaction conditions were applied:
94° C.×1 minute (PAD)
94° C.×30 seconds (Denaturation)
55° C.×30 seconds (Annealing to template)
72° C.×1 minute (Primer elongation)

A cycle consisting of the above 3 steps was repeated 30 times.
72° C.×7 minutes (Final elongation)
4° C. (Retention)

An amplified band with a size of approximately 1,000 bp was cut out and purified by agarose gel electrophoresis, and was then subcloned into the BamHI-EcoRI site of a pRSET vector (Invitrogen). Thereafter, it was expressed in *Escherichia coli* (JM109-DE3). However, whatever it may be derived from an orange individual or red individual, the protein expressed in the *Escherichia coli* did not emit fluorescence.

It was found that proteins translated from the genes cloned herein (a translated protein derived from an orange individual is referred to as Kusabira-Orange, and a translated protein derived from a red individual is referred to as Kusabira-Cyan) lack about 10 amino acids at their N-terminus, when compared with the known fluorescent proteins (FP486 and Azami-Green) (Table 1). Accordingly, 2 types of segments each consisting of about 10 amino acids were added to their N-termini.

TABLE 1

Comparison of amino acid sequences at N-termini among the fluorescent proteins

Fluorescent proteins derived from orange individuals

↓

Kusabira-Orange-1 (KO-1)     MSVIKPE*MKMKYFMDGSVNGHEFTVEGEG*...
(Residues 1-29 of SEQ ID NO: 3)

TABLE 1-continued

Comparison of amino acid sequences at N-termini
among the fluorescent proteins

```
        -Orange-2 (KO-2)    MALSNKFIGDDMKMKYFMDGSVNGHEFTVEGEG...
                            (Residues 1-33 of SEQ ID NO: 4)

Fluorescent proteins derived from red individuals

Kusabira-Cyan-1 (KCy-1)       MSVIKPEMKMKYFMDGSVNGHFETVEGEG...
                            (Residues 1-29 of SEQ ID NO: 1)
        -Cyan-2 (KCy-2)     MALSNKFIGDDMKMKYFMDGSVNGHEFTVEGEG...
                            (Residues 1-33 of SEQ ID NO: 2)
Azami-Green                   MSVIKPEMKIKLCMRGTVNGHNFVIEGEG...
                            (SEQ ID NO: 22)
FP486                         MALSNKFIGDDMKMTYHMDGCVNGHYFTVEGEG...
                            (SEQ ID NO: 23)
```

The sequence portions of Kusabira-Orange and Kusabira-Cyan indicated with italicized letters (from the letters pointed with an arrow and downward) have been cloned.

In one case, 11 amino acids (MALSNKFIGDD) (Residues 1-11 of SEQ ID NO: 23) at the N-terminus of FP486 were used, the amino acid sequence as a whole of which is similar to those of the above fluorescent proteins. In another case, 7 amino acids (MSVIKPE) (Residues 1-7 of SEQ ID NO: 22) at the N-terminus of Azami-Green were used, which had previously been cloned. As a result, it was found that, in both cases where either one of the above amino acid sequences was added, orange fluorescence was emitted from a fluorescent protein derived from an orange individual, and that cyan fluorescence was emitted from a fluorescent protein derived from a red individual. A fluorescent protein produced by adding the 7 amino acids at the N-terminus of Azami-Green to a fluorescent protein derived from an orange individual was defined as Kusabira-Orange-1 (KO-1) (SEQ ID NO: 3), and a fluorescent protein produced by adding the 11 amino acids at the N-terminus of FP486 to a fluorescent protein derived from an orange individual was defined as Kusabira-Orange-2 (KO-2) (SEQ ID NO: 4). A fluorescent protein produced by adding the 7 amino acids at the N-terminus of Azami-Green to a fluorescent protein derived from a red individual was defined as Kusabira-Cyan-1 (KCy-1) (SEQ ID NO: 1), and a fluorescent protein produced by adding the 11 amino acids at the N-terminus of FP486 to a fluorescent protein derived from a red individual was defined as Kusabira-Cyan-2 (KCy-2) (SEQ ID NO: 2).

The entire nucleotide sequences of KCy-1, KCy-2, KO-1 and KO-2 are shown in SEQ ID NOS: 5 to 8, respectively.

The above 4 types of proteins were constructed such that His-tag was attached to their N-terminus. Thus, the expressed proteins were purified with Ni-Agarose gel (QIAGEN). Purification was carried out in accordance with protocols attached with the above product. Subsequently, the properties of the purified proteins were analyzed.

(8) Analysis of Fluorescence Properties

An absorption spectrum was measured using a 20 μM fluorescent protein and a 50 mM HEPES solution of pH 7.5. A molar absorption coefficient was calculated from the value of the peak of this spectrum. In the case of each of KCy-1 and KCy-2, the fluorescent protein was diluted with the above buffer solution such that its absorption peak was observed at 455 nm and that its absorption at 400 nm became 0.005. Thereafter, a fluorescence spectrum obtained by excitation at 400 nm and an excitation spectrum obtained by fluorescence at 520 nm were determined. Likewise, ECFP (Clontech) was diluted with the above buffer solution such that its absorption at 400 nm became 0.005, and its fluorescence spectrum was determined. Setting the quantum yield of ECFP at 0.4, the quantum yield of each of KCy-1 and KCy-2 was obtained. In the case of each of KO-1 and KO-2, the fluorescent protein was diluted with the above buffer solution such that its absorption peak was observed at 548 nm and that its absorption at 500 nm became 0.0025. Thereafter, a fluorescence spectrum obtained by excitation at 500 nm and an excitation spectrum obtained by fluorescence at 590 nm were determined. Likewise, DsRed (Clontech) was diluted with the above buffer solution such that its absorption at 500 nm became 0.0025, and its fluorescence spectrum was determined. Setting the quantum yield of DsRed at 0.29, the quantum yield of each of KO-1 and KO-2 was obtained. The results are shown in Table 2 and FIG. 1.

TABLE 2

|   | Excitation maximum | Fluorescence maximum | Molar absorption coefficient | Quantum yield | pH stability | Number of amino acids |
|---|---|---|---|---|---|---|
| Comparison of Kusabira-Cyan with ECFP (Clontech) | | | | | | |
| KCy-1 | 455 nm | 488 nm | 38,700 (455 nm) | 0.85 | Stable at pH 5 to 9 | 223 |
| KCy-2 | 455 nm | 488 nm | 27,700 (455 nm) | 0.81 | Stable at pH 5 to 9 | 227 |
| ECFP | 435 nm | 478 nm | 28,750 (435 nm) | 0.40 | pKa = 5.5 | 239 |
| Comparison of Kusabira-Orange with DsRed (Clontech) | | | | | | |
| KO-1 | 548 nm | 561 nm | 75,900 (548 nm) | 0.44 | pKa <5.0 | 217 |

TABLE 2-continued

|       | Excitation maximum | Fluorescence maximum | Molar absorption coefficient | Quantum yield | pH stability | Number of amino acids |
|-------|--------------------|-----------------------|-------------------------------|---------------|--------------|------------------------|
| KO-2  | 548 nm             | 561 nm                | 51,000 (548 nm)               | 0.50          | pKa <5.0     | 221                    |
| DsRed | 559 nm             | 583 nm                | 86,100 (559 nm)               | 0.29          | None         | 226                    |

Figure 2:
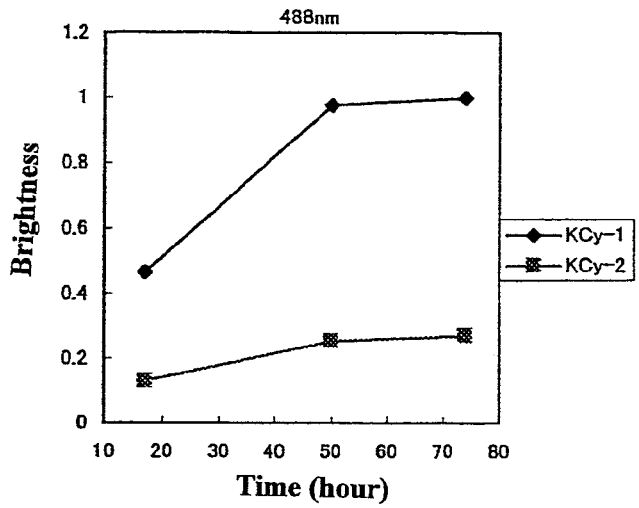
FIG. 2 shows results obtained by analyzing the fluorescent properties of the fluorescent proteins KCy-1, KCy-2, KO-1 and KO-2 derived from *Fungia* sp. of the present invention.
(1) Difference in coloration between Kcy-1 and Kcy-2 in *Escherichia coli* (Fluorescence at 488 nm obtained by excitation at 400 nm)
(2) Difference in coloration between KO-1 and KO-2 in *Escherichia coli* (Fluorescence at 561 nm obtained by excitation at 500 nm)
(3) Change in fluorescence between KO-1 and KO-2 (The value (maturation value) of orange components (561 nm)/ green components (508 nm) obtained by excitation at 470 nm)
Figure 2:
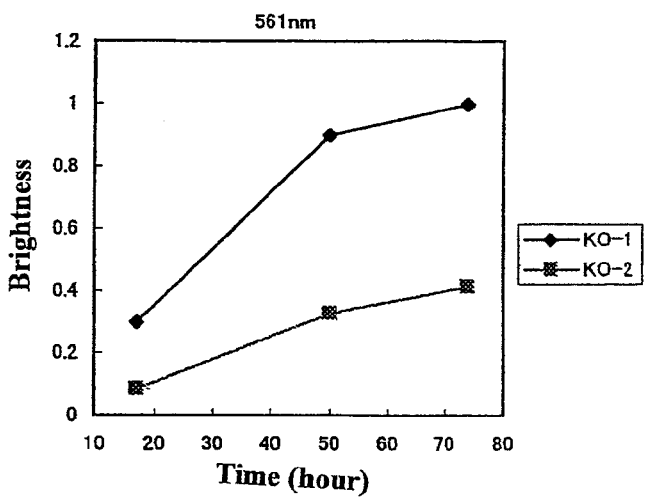
Figure 2:
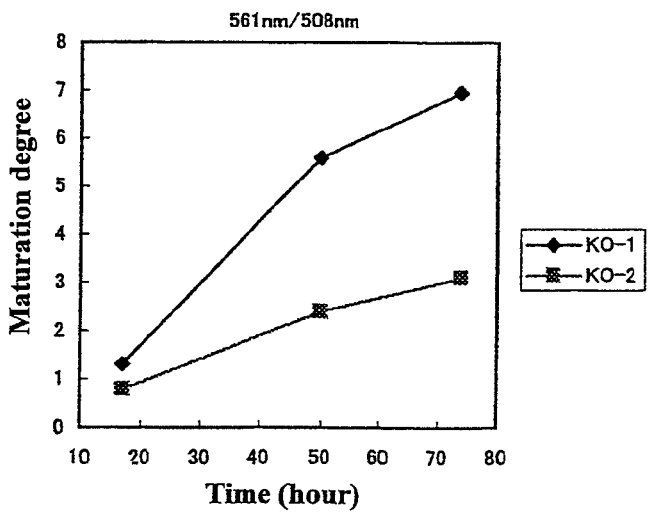
Figure 3:
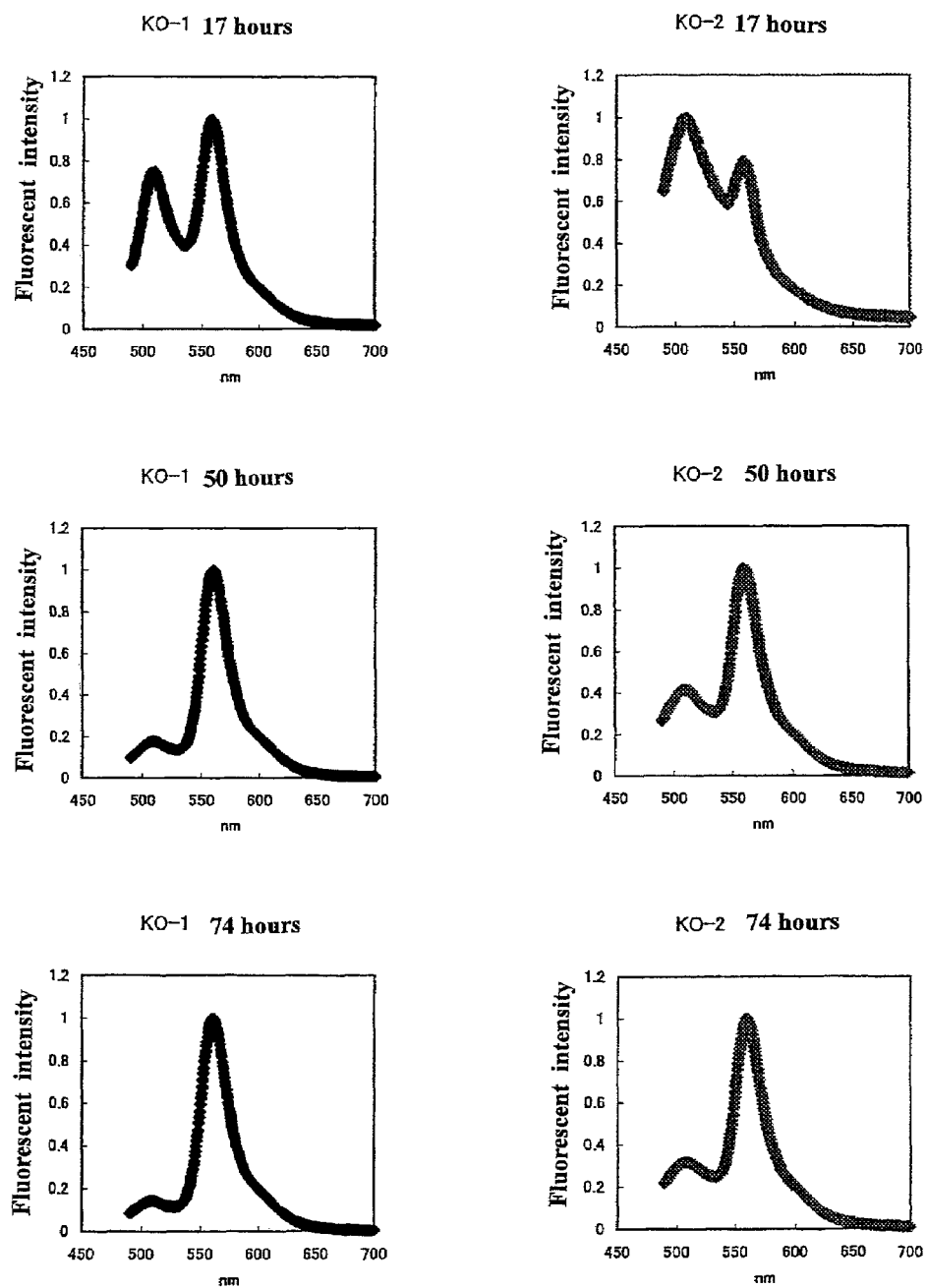
FIG. 3 shows the change over time in the green components (508 nm) and orange components (561 nm) in fluorescent proteins (KO-1 and KO-2) derived from *Fungia* sp. of the present invention.

(9) Difference in Expression Caused by Difference of Amino Acid Sequence at N-terminus The above each protein was expressed in *Escherichia coli* (JM109-DE3). 0.1 mM IPTG was used to induce the expression of the protein, and sampling was then carried out thereon at 17 hours, 50 hours, and 74 hours after the expression induction. Thereafter, a change in the fluorescence spectrum was analyzed with a fluorospectrophotometer. The results are shown in FIGS. 2 and 3. The appearance of fluorescence was different depending on an amino acid sequence added to the N-terminus. In both cases of Kusabira-Orange and Kusabira-Cyan, a protein to which the 7 amino acids at the N-terminus of an Azami-Green (*Galaxea fascicularis* fluorescent protein) were added, emitted fluorescence more rapidly than the other did.

In the cases of KO-1 and KO-2, green fluorescence was first emitted, and it was then changed to orange fluorescence. Such a maturation process was carried out more rapidly in KO-1 than in KO-2.

(10) Measurement of pH Sensitivity

Figure 4:
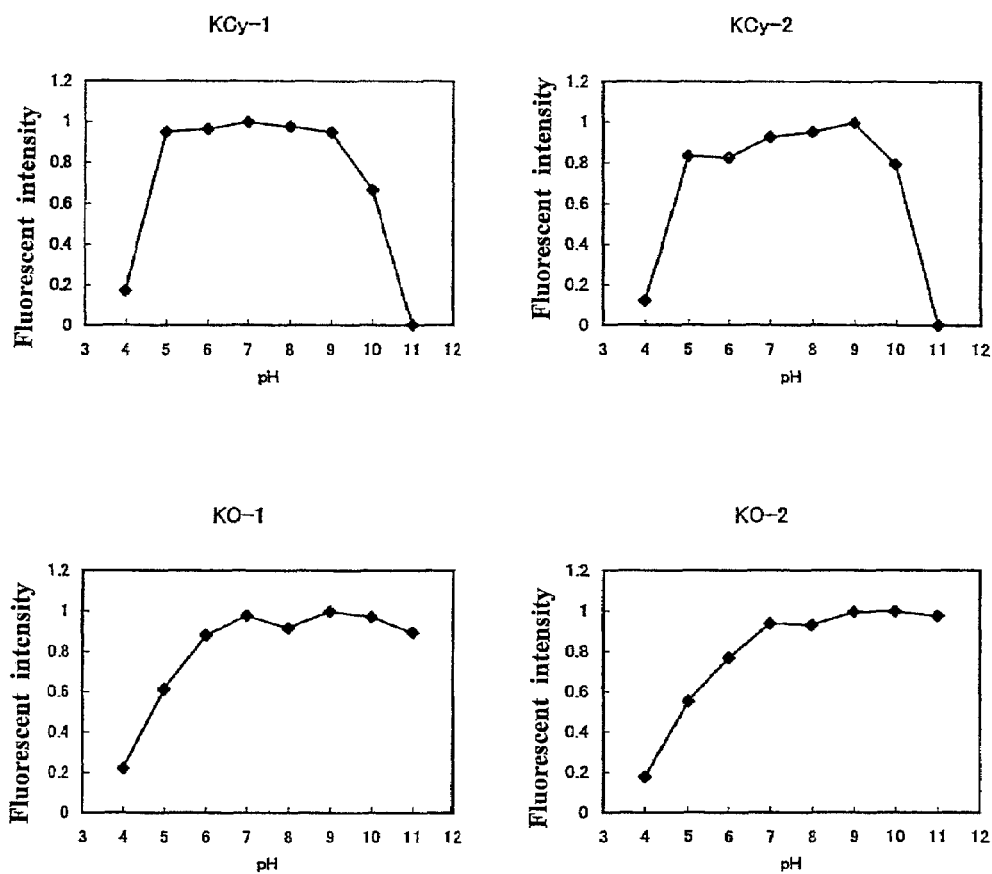
FIG. 4 shows the pH sensitivity of the fluorescence intensity of each of the fluorescent proteins (KCy-1, KCy-2, KO-1 and KO-2) derived from *Fungia* sp. of the present invention.

In the cases of KCy-1 and KCy-2, the fluorescent protein was diluted with the following buffer such that the absorption at 400 nm became 0.005. In the cases of KO-1 and KO-2, the fluorescent protein was diluted with the following buffer such that the absorption at 500 nm became 0.0025. Then, the fluorescence spectrums were measured. The measurement results are shown in FIG. 4.
pH 4 and 5: Acetate buffer
pH 6: MES buffer
pH 7: MOPS buffer
pH 8: HEPES buffer
pH 9 and 10: Glycine buffer
pH 11: Phosphate buffer Example 2

Production of Amino Acid-Substituted Mutant of Kusabira-Orange (KO)

Figure 5:
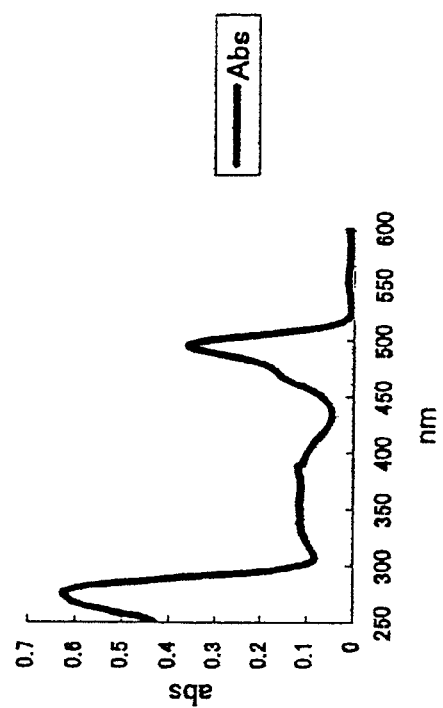
FIG. 5 shows the fluorescence spectrum (em) and excitation spectrum (ex) (left figure), and absorption spectrum (right figure) of a mutant (KO-C64A) of a fluorescent protein derived from *Fungia* sp. of the present invention.
Figure 5:
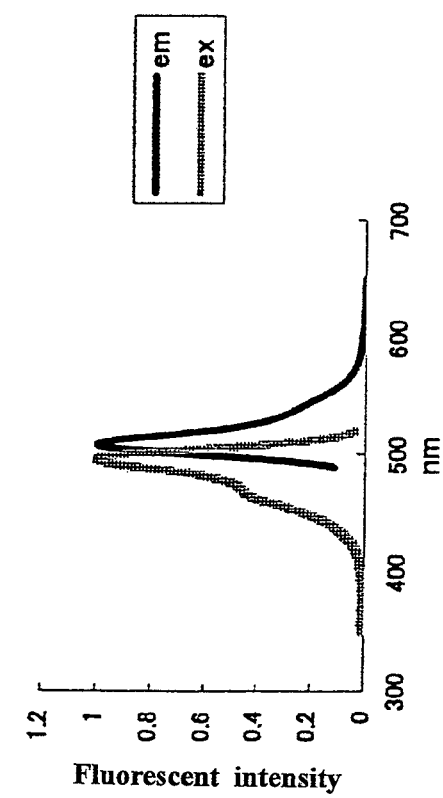
Figure 6:
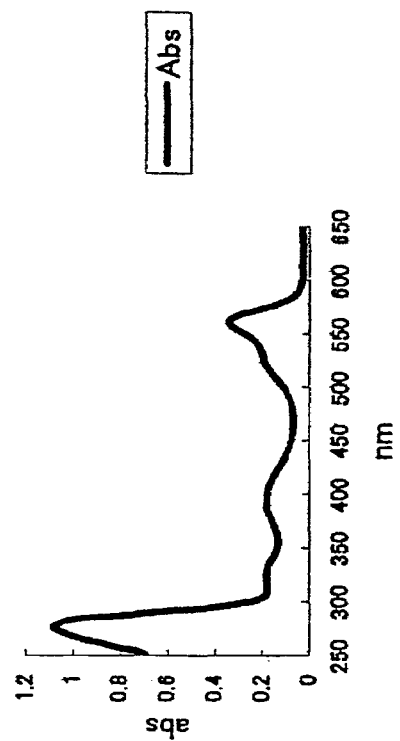
FIG. 6 shows the fluorescence spectrum (em) and excitation spectrum (ex) (left figure), and absorption spectrum (right figure) of a mutant (KO-E211A) of a fluorescent protein derived from *Fungia* sp. of the present invention.
Figure 6:
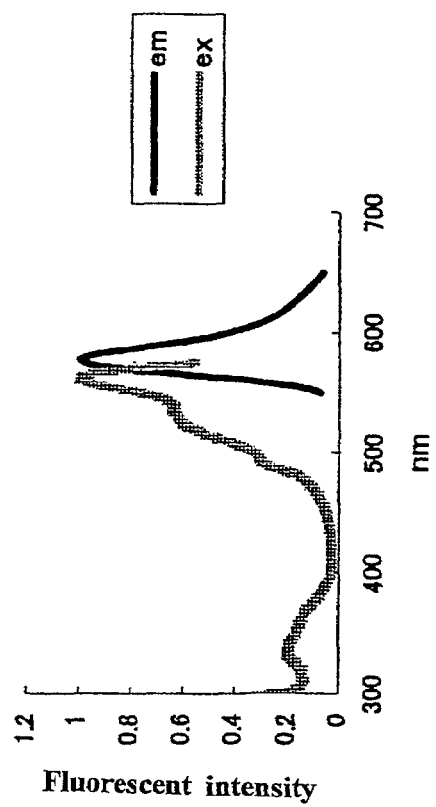

Kusabira-Orange (KO) is a fluorescent protein which emits orange fluorescence (fluorescence maximum at 561 mm, and excitation maximum at 548 nm). Cysteine at position 64 was substituted by alanine in the amino acid sequence of KO-1, so as to obtain a mutant which emits green fluorescence (fluorescence maximum at 508 nm, and excitation maximum at 496 nm), wherein fluorescent properties were sifted on the short wavelength side when compared with KO (FIG. 5). Moreover, glutamic acid at position 211 was substituted by alanine in the amino acid sequence of KO-1, so as to obtain a mutant which emits red fluorescence (fluorescence maximum at 578 nm, and excitation maximum at 563 nm), wherein fluorescent properties were sifted on the long wavelength side when compared with KO (FIG. 6).

INDUSTRIAL APPLICABILITY

The present invention provides novel fluorescent proteins derived from organisms other than a jellyfish. Since the fluorescent proteins of the present invention have desired fluorescent properties and has low pH sensitivity, it is useful in the molecular biological analysis.

What is claimed:

1. An isolated DNA which encodes the protein of the following (a) or (b):
   (a) a protein having the amino acid sequence shown in SEQ ID NO: 1; or
   (b) a protein having an amino acid sequence comprising a deletion, substitution and/or addition of one to eleven amino acids with respect to the amino acid sequence shown in SEQ ID NO: 1, and having an excitation wavelength and fluorescent wavelength which are equivalent to the excitation wavelength and fluorescent wavelength of a protein having the amino acid sequence shown in SEQ ID NO: 1.

2. A recombinant vector having the isolated DNA of claim 1.

3. An isolated transformant having the isolated DNA of claim 1.

4. A fluorescent reagent kit which comprises a fluorescent protein encoded by the isolated DNA of claim 1, the isolated DNA which encodes the protein of claim 1, a recombinant vector having the isolated DNA of claim 1, an isolated transformant having the isolated DNA of claim 1, or a fusion fluorescent protein consisting of a fluorescent protein encoded by the insolated DNA of claim 1 and another protein.

5. An isolated DNA of the following (a) or (b):
   a) isolated DNA having the nucleotide sequence shown in SEQ ID NO: 5; or
   b) isolated DNA having a nucleotide sequence comprising a deletion, substitution and/or addition of one to thirty three nucleotides with respect of the nucleotide sequence shown in SEQ ID NO: 5, and encoding a protein having an excitation wavelength and fluorescent wavelength which are equivalent to the excitation wavelength and fluorescent wavelength of a protein encoded by the nucleotide sequence shown in SEQ ID NO: 5.

6. A recombinant vector having the isolated DNA of claim 5.

7. An isolated transformant having the isolated DNA of claim 5.

8. A fluorescent reagent kit which comprises a fluorescent protein encoded by the isolated DNA of claim 5, the isolated DNA which encodes the protein of claim 5, a recombinant vector having the isolated DNA of claim 5, an isolated transformant having the isolated DNA of claim 5, or a fusion fluorescent protein consisting of a fluorescent protein encoded by the insolated DNA of claim 5 and another protein.

* * * * *

UNITED STATES PATENT AND TRADEMARK OFFICE
CERTIFICATE OF CORRECTION

PATENT NO. : 7,541,451 B2  Page 1 of 1
APPLICATION NO. : 11/739133
DATED : June 2, 2009
INVENTOR(S) : A. Miyawaki et al.

It is certified that error appears in the above-identified patent and that said Letters Patent is hereby corrected as shown below:

At column 33, line 46 (claim 4, line 7) of the printed patent, "insolated" should be --isolated--.

At column 34, line 44 (claim 8, line 7) of the printed patent, "insolated" should be --isolated--.

Signed and Sealed this

Fifth Day of January, 2010

David J. Kappos
*Director of the United States Patent and Trademark Office*

SEQUENCE LISTING

```
<160> NUMBER OF SEQ ID NOS: 21

<210> SEQ ID NO 1
<211> LENGTH: 223
<212> TYPE: PRT
<213> ORGANISM: Fungia sp.

<400> SEQUENCE: 1

Met Ser Val Ile Lys Pro Glu Met Lys Met Lys Tyr Phe Met Asp Gly
1               5                   10                  15

Ser Val Asn Gly His Glu Phe Thr Val Glu Gly Glu Gly Thr Gly Lys
            20                  25                  30

Pro Tyr Glu Gly Lys His Lys Ile Thr Leu Asp Val Thr Lys Gly Gly
        35                  40                  45

Pro Leu Pro Phe Ala Phe Asp Leu Leu Ser Thr Val Phe Ser Tyr Gly
    50                  55                  60

Asn Arg Cys Leu Thr Lys Tyr Pro Asp Asp Ile Pro Asp Tyr Phe Lys
```

```
            65                  70                  75                  80
Gln Cys Phe Pro Gly Gly Tyr Ser Trp Glu Arg Lys Phe Glu Phe Glu
                85                  90                  95

Asp Gly Gly Leu Ala Ile Ala Lys Ala Glu Ile Ser Leu Lys Gly Asn
            100                 105                 110

Cys Phe Glu His Lys Ser Thr Ile Glu Gly Thr Phe Pro Asp Ser Ser
            115                 120                 125

Pro Ile Ala Gln Asn Lys Thr Leu Gly Trp Glu Pro Ser Thr Glu Lys
        130                 135                 140

Met Thr Val Arg Asp Gly Ser Met Lys Gly Asp Asp Ala Ala Tyr Leu
145                 150                 155                 160

Lys Leu Val Gly Gly Gly Asn His Lys Cys Tyr Phe Thr Thr Thr Tyr
                165                 170                 175

Thr Ala Lys Lys Lys Ile Pro Asn Leu Pro Gln Ser His Phe Ile Gly
            180                 185                 190

His Arg Ile Ser Ser Val Val Asn Gly Thr Lys Ile Gly Val Met Glu
            195                 200                 205

Asp Ala Ile Ala His Leu Tyr Pro Phe Asn Gly Val Pro Cys Gln
        210                 215                 220

<210> SEQ ID NO 2
<211> LENGTH: 227
<212> TYPE: PRT
<213> ORGANISM: Fungia sp.

<400> SEQUENCE: 2

Met Ala Leu Ser Asn Lys Phe Ile Gly Asp Asp Met Lys Met Lys Tyr
1               5                   10                  15

Phe Met Asp Gly Ser Val Asn Gly His Glu Phe Thr Val Glu Gly Glu
            20                  25                  30

Gly Thr Gly Lys Pro Tyr Glu Gly Lys His Lys Ile Thr Leu Asp Val
        35                  40                  45

Thr Lys Gly Gly Pro Leu Pro Phe Ala Phe Asp Leu Leu Ser Thr Val
    50                  55                  60

Phe Ser Tyr Gly Asn Arg Cys Leu Thr Lys Tyr Pro Asp Asp Ile Pro
65                  70                  75                  80

Asp Tyr Phe Lys Gln Cys Phe Pro Gly Gly Tyr Ser Trp Glu Arg Lys
                85                  90                  95

Phe Glu Phe Glu Asp Gly Gly Leu Ala Ile Ala Lys Ala Glu Ile Ser
            100                 105                 110

Leu Lys Gly Asn Cys Phe Glu His Lys Ser Thr Ile Glu Gly Thr Phe
            115                 120                 125

Pro Asp Ser Ser Pro Ile Ala Gln Asn Lys Thr Leu Gly Trp Glu Pro
        130                 135                 140

Ser Thr Glu Lys Met Thr Val Arg Asp Gly Ser Met Lys Gly Asp Asp
145                 150                 155                 160

Ala Ala Tyr Leu Lys Leu Val Gly Gly Gly Asn His Lys Cys Tyr Phe
                165                 170                 175

Thr Thr Thr Tyr Thr Ala Lys Lys Lys Ile Pro Asn Leu Pro Gln Ser
            180                 185                 190

His Phe Ile Gly His Arg Ile Ser Ser Val Val Asn Gly Thr Lys Ile
            195                 200                 205

Gly Val Met Glu Asp Ala Ile Ala His Leu Tyr Pro Phe Asn Gly Val
        210                 215                 220
```

```
Pro Cys Gln
225

<210> SEQ ID NO 3
<211> LENGTH: 217
<212> TYPE: PRT
<213> ORGANISM: Fungia sp.

<400> SEQUENCE: 3

Met Ser Val Ile Lys Pro Glu Met Lys Met Lys Tyr Phe Met Asp Gly
1               5                   10                  15

Ser Val Asn Gly His Glu Phe Thr Val Glu Gly Glu Gly Thr Gly Lys
            20                  25                  30

Pro Tyr Glu Gly His Gln Glu Met Thr Leu Arg Val Thr Met Ala Lys
        35                  40                  45

Gly Gly Pro Met Pro Phe Ser Phe Asp Leu Val Ser His Thr Phe Cys
    50                  55                  60

Tyr Gly His Arg Pro Phe Thr Lys Tyr Pro Glu Ile Pro Asp Tyr
65                  70                  75                  80

Phe Lys Gln Ala Phe Pro Glu Gly Leu Ser Trp Glu Arg Ser Leu Gln
                85                  90                  95

Phe Glu Asp Gly Gly Phe Ala Ala Val Ser Ala His Ile Ser Leu Arg
            100                 105                 110

Gly Asn Cys Phe Glu His Lys Ser Lys Phe Val Gly Val Asn Phe Pro
        115                 120                 125

Ala Asp Gly Pro Val Met Gln Asn Gln Ser Ser Asp Trp Glu Pro Ser
    130                 135                 140

Thr Glu Lys Ile Thr Thr Cys Asp Gly Val Leu Lys Gly Asp Val Thr
145                 150                 155                 160

Met Phe Leu Lys Leu Ala Gly Gly Asn His Lys Cys Gln Phe Lys
                165                 170                 175

Thr Thr Tyr Lys Ala Ala Lys Lys Ile Leu Lys Met Pro Gln Ser His
            180                 185                 190

Phe Ile Gly His Arg Leu Val Arg Lys Thr Glu Gly Asn Ile Thr Glu
        195                 200                 205

Leu Val Glu Asp Ala Val Ala His Cys
    210                 215

<210> SEQ ID NO 4
<211> LENGTH: 221
<212> TYPE: PRT
<213> ORGANISM: Fungia sp.

<400> SEQUENCE: 4

Met Ala Leu Ser Asn Lys Phe Ile Gly Asp Asp Met Lys Met Lys Tyr
1               5                   10                  15

Phe Met Asp Gly Ser Val Asn Gly His Glu Phe Thr Val Glu Gly Glu
            20                  25                  30

Gly Thr Gly Lys Pro Tyr Glu Gly His Gln Glu Met Thr Leu Arg Val
        35                  40                  45

Thr Met Ala Lys Gly Gly Pro Met Pro Phe Ser Phe Asp Leu Val Ser
    50                  55                  60

His Thr Phe Cys Tyr Gly His Arg Pro Phe Thr Lys Tyr Pro Glu Glu
65                  70                  75                  80

Ile Pro Asp Tyr Phe Lys Gln Ala Phe Pro Glu Gly Leu Ser Trp Glu
                85                  90                  95
```

```
Arg Ser Leu Gln Phe Glu Asp Gly Gly Phe Ala Ala Val Ser Ala His
            100                 105                 110
Ile Ser Leu Arg Gly Asn Cys Phe Glu His Lys Ser Lys Phe Val Gly
        115                 120                 125
Val Asn Phe Pro Ala Asp Gly Pro Val Met Gln Asn Gln Ser Ser Asp
    130                 135                 140
Trp Glu Pro Ser Thr Glu Lys Ile Thr Thr Cys Asp Gly Val Leu Lys
145                 150                 155                 160
Gly Asp Val Thr Met Phe Leu Lys Leu Ala Gly Gly Asn His Lys
                165                 170                 175
Cys Gln Phe Lys Thr Thr Tyr Lys Ala Ala Lys Lys Ile Leu Lys Met
            180                 185                 190
Pro Gln Ser His Phe Ile Gly His Arg Leu Val Arg Lys Thr Glu Gly
        195                 200                 205
Asn Ile Thr Glu Leu Val Glu Asp Ala Val Ala His Cys
    210                 215                 220

<210> SEQ ID NO 5
<211> LENGTH: 672
<212> TYPE: DNA
<213> ORGANISM: Fungia sp.

<400> SEQUENCE: 5
atgagtgtga ttaaaccaga gatgaagatg aagtacttca tggacggatc cgtcaatggg      60
catgagttca gagttgaagg tgaaggcaca ggcaaaccct tacgagggaa agcacaaaata    120
acacttgacg tcaccaaggg tgggccactg ccttttgcgt ttgacttgtt gtctacagtg    180
ttctcttatg gcaacagatg ccttactaaa tatcctgacg atatccccga ctatttcaaa    240
caatgctttc ctggaggcta ttcatgggaa agaaagtttg agttcgaaga tggcgggttg    300
gctatagcca aagcggaaat aagccttaaa ggaaactgct cgaacacaa atccaccatt     360
gaaggcactt ttcccgatag cagtcctatt gcgcaaaaca agacgctagg atgggaacca    420
tccaccgaga gatgaccgt ccgcgacgga tcaatgaagg gtgatgatgc ggcctacctc     480
aaattggtgg gaggcggcaa tcacaaatgc tactttacaa ctacctacac agcgaagaaa    540
aagattccta acctgccaca aagccatttc attgggcatc gcatctccag tgtcgtcaat    600
ggcactaaaa ttggagtgat ggaagatgca attgctcatc tttaccccttt taatggcgtg    660
ccatgccagt ga                                                        672

<210> SEQ ID NO 6
<211> LENGTH: 684
<212> TYPE: DNA
<213> ORGANISM: Fungia sp.

<400> SEQUENCE: 6
atggccctga gcaacaagtt catcggggac gacatgaaga tgaagtactt catggacgga      60
tccgtcaatg ggcatgagtt cacagttgaa ggtgaaggca caggcaaacc ttacgaggga    120
aagcacaaaa taacacttga cgtcaccaag ggtgggccac tgccttttgc gtttgacttg    180
ttgtctacag tgttctctta tggcaacaga tgccttacta aatatcctga cgatatcccc    240
gactatttca acaatgcttt cctggaggc tattcatggg aaagaaagtt tgagttcgaa     300
gatggcgggt tggctatagc caaagcggaa ataagcctta aaggaaactg cttcgaacac    360
aaaatccacca ttgaaggcac ttttcccgat agcagtccta ttgcgcaaaa caagacgcta    420
ggatgggaac catccaccga agatgacc gtccgcgacg gatcaatgaa gggtgatgat     480
```

```
gcggcctacc tcaaattggt gggaggcggc aatcacaaat gctactttac aactacctac    540
acagcgaaga aaaagattcc taacctgcca caaagccatt tcattgggca tcgcatctcc    600
agtgtcgtca atggcactaa aattggagtg atggaagatg caattgctca tctttaccct    660
tttaatggcg tgccatgcca gtga                                           684
```

<210> SEQ ID NO 7
<211> LENGTH: 654
<212> TYPE: DNA
<213> ORGANISM: Fungia sp.

<400> SEQUENCE: 7

```
atgagtgtga ttaaaccaga gatgaagatg aagtacttca tggacggatc cgtcaatggg     60
catgagttca cagttgaagg tgaaggcaca ggcaaaccct acgagggaca tcaagagatg    120
acactacgcg tcacaatggc caagggcggg ccaatgcctt ctcgtttga cttagtgtca    180 cacacgttct gttacggcca cagacctttt actaaatatc cagaagagat accagactat    240
ttcaaacaag catttcctga aggcctgtca tgggaaggt cgttgcagtt cgaagatggt    300
gggtttgctg cagtcagtgc gcatataagc cttagaggaa actgcttcga gcacaaatcc    360
aaatttgttg gggttaactt tcctgccgat ggtcctgtga tgcaaaacca aagttctgat    420
tgggagccat caaccgagaa aattactacc tgcgacggag ttctgaaggg tgatgttacg    480
atgttcctaa gcttgcgggg aggcggcaat cacaaatgcc aattcaagac tacttacaag    540
gcggcaaaaa agattcttaa aatgccacaa agccatttca tcgggcatcg cctcgtcagg    600
aaaaccgaag gcaacattac tgagctggta gaagatgcag tagctcattg ctga          654
```

<210> SEQ ID NO 8
<211> LENGTH: 666
<212> TYPE: DNA
<213> ORGANISM: Fungia sp.

<400> SEQUENCE: 8

```
atggccctga gcaacaagtt catcggggac gacatgaaga tgaagtactt catggacgga     60
tccgtcaatg ggcatgagtt cacagttgaa ggtgaaggca caggcaaacc ttacgaggga    120
catcaagaga tgacactacg cgtcacaatg gccaagggcg ggccaatgcc tttctcgttt    180
gacttagtgt cacacacgtt ctgttacggc cacagacctt ttactaaata tccagaagag    240
ataccagact atttcaaaca agcatttcct gaaggcctgt catgggaaag gtcgttgcag    300
ttcgaagatg gtgggtttgc tgcagtcagt gcgcatataa gccttagagg aaactgcttc    360
gagcacaaat ccaaatttgt tggggttaac tttcctgccg atggtcctgt gatgcaaaac    420
caaagttctg attgggagcc atcaaccgag aaaattacta cctgcgacgg agttctgaag    480
ggtgatgtta cgatgttcct aaagcttgcg ggaggcggca atcacaaatg ccaattcaag    540
actacttaca aggcggcaaa aagattcttaaaatgccac aaagccattt catcgggcat    600
cgcctcgtca ggaaaaccga aggcaacatt actgagctgg tagaagatgc agtagctcat    660
tgctga                                                               666
```

<210> SEQ ID NO 9
<211> LENGTH: 21
<212> TYPE: DNA
<213> ORGANISM: Artificial
<220> FEATURE:
<223> OTHER INFORMATION: Synthetic DNA

<400> SEQUENCE: 9
gaaggrtgyg tcaayggrca y                                    21

<210> SEQ ID NO 10
<211> LENGTH: 23
<212> TYPE: DNA
<213> ORGANISM: Artificial
<220> FEATURE:
<223> OTHER INFORMATION: Synthetic DNA

<400> SEQUENCE: 10
acvggdccat ydgvaagaaa rtt                                  23

<210> SEQ ID NO 11
<211> LENGTH: 36
<212> TYPE: DNA
<213> ORGANISM: Artificial
<220> FEATURE:
<223> OTHER INFORMATION: Synthetic DNA
<220> FEATURE:
<221> NAME/KEY: n
<222> LOCATION: (24)..(35)
<223> OTHER INFORMATION: n is inosine
<220> FEATURE:
<221> NAME/KEY: misc_feature
<222> LOCATION: (24)..(25)
<223> OTHER INFORMATION: n is inosine
<220> FEATURE:
<221> NAME/KEY: misc_feature
<222> LOCATION: (29)..(30)
<223> OTHER INFORMATION: n is inosine
<220> FEATURE:
<221> NAME/KEY: misc_feature
<222> LOCATION: (34)..(35)
<223> OTHER INFORMATION: n is inosine

<400> SEQUENCE: 11
ggccacgcgt cgactagtac gggnngggnn gggnng                    36

<210> SEQ ID NO 12
<211> LENGTH: 22
<212> TYPE: DNA
<213> ORGANISM: Artificial
<220> FEATURE:
<223> OTHER INFORMATION: Synthetic DNA

<400> SEQUENCE: 12
ggcttatatg cgcactgact gc                                   22

<210> SEQ ID NO 13
<211> LENGTH: 20
<212> TYPE: DNA
<213> ORGANISM: Artificial
<220> FEATURE:
<223> OTHER INFORMATION: Synthetic DNA

<400> SEQUENCE: 13
ggccacgcgt cgactagtac                                      20

<210> SEQ ID NO 14
<211> LENGTH: 21
<212> TYPE: DNA
<213> ORGANISM: Artificial
<220> FEATURE:
<223> OTHER INFORMATION: Synthetic DNA

<400> SEQUENCE: 14
tatctcttca ggatatttag t                                    21

<210> SEQ ID NO 15
<211> LENGTH: 36
<212> TYPE: DNA
<213> ORGANISM: Artificial
<220> FEATURE:
<223> OTHER INFORMATION: Synthetic DNA
<220> FEATURE:
<221> NAME/KEY: n
<222> LOCATION: (24)..(35)
<223> OTHER INFORMATION: n is inosine
<220> FEATURE:
<221> NAME/KEY: misc_feature
<222> LOCATION: (24)..(25)
<223> OTHER INFORMATION: n is inosine
<220> FEATURE:
<221> NAME/KEY: misc_feature
<222> LOCATION: (29)..(30)
<223> OTHER INFORMATION: n is inosine
<220> FEATURE:
<221> NAME/KEY: misc_feature
<222> LOCATION: (34)..(35)
<223> OTHER INFORMATION: n is inosine

<400> SEQUENCE: 15
ggccacgcgt cgactagtac gggnngggnn gggnng                        36

<210> SEQ ID NO 16
<211> LENGTH: 20
<212> TYPE: DNA
<213> ORGANISM: Artificial
<220> FEATURE:
<223> OTHER INFORMATION: Synthetic DNA

<400> SEQUENCE: 16
gggaaaagtg ccttcaatgg                                          20

<210> SEQ ID NO 17
<211> LENGTH: 20
<212> TYPE: DNA
<213> ORGANISM: Artificial
<220> FEATURE:
<223> OTHER INFORMATION: Synthetic DNA

<400> SEQUENCE: 17
ggccacgcgt cgactagtac                                          20

<210> SEQ ID NO 18
<211> LENGTH: 20
<212> TYPE: DNA
<213> ORGANISM: Artificial
<220> FEATURE:
<223> OTHER INFORMATION: Synthetic DNA

<400> SEQUENCE: 18
tcttcgaact caaactttct                                          20

<210> SEQ ID NO 19
<211> LENGTH: 22
<212> TYPE: DNA
<213> ORGANISM: Artificial
<220> FEATURE:
<223> OTHER INFORMATION: Synthetic DNA

<400> SEQUENCE: 19
gcagtcagtg cgcatataag cc                                       22

<210> SEQ ID NO 20

```
<211> LENGTH: 20
<212> TYPE: DNA
<213> ORGANISM: Artificial
<220> FEATURE:
<223> OTHER INFORMATION: Synthetic DNA

<400> SEQUENCE: 20
ccattgaagg cacttttccc                                               20

<210> SEQ ID NO 21
<211> LENGTH: 34
<212> TYPE: DNA
<213> ORGANISM: Artificial
<220> FEATURE:
<223> OTHER INFORMATION: Synthetic DNA

<400> SEQUENCE: 21
cgggatccat gaagatgaag tactttatgg atgg                               34
```